United States Patent [19]

Das et al.

[11] Patent Number: 4,536,514

[45] Date of Patent: Aug. 20, 1985

[54] 7-OXABICYCLOHEPTANE SUBSTITUTED PROSTAGLANDIN ANALOGS USEFUL IN THE TREATMENT OF THROMBOLYTIC DISEASE

[75] Inventors: Jagabandhu Das, Plainsboro; Martin F. Haslanger, Lambertville, both of N.J.

[73] Assignee: E. R. Squibb & Sons, Inc., Princeton, N.J.

[21] Appl. No.: 597,324

[22] Filed: Apr. 6, 1984

[51] Int. Cl.$^3$ .................. A61K 31/34; A61K 31/557; C07D 307/00
[52] U.S. Cl. ..................................... 514/469; 549/463
[58] Field of Search ......................... 549/463; 424/285

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0043292 8/1982 European Pat. Off. .
2039909 8/1980 United Kingdom .

Primary Examiner—Henry R. Jiles
Assistant Examiner—Bernard I. Dentz
Attorney, Agent, or Firm—Lawrence S. Levinson; Burton Rodney

[57] ABSTRACT

7-Oxabicycloheptane substituted prostaglandin analogs are provided having the structural formula

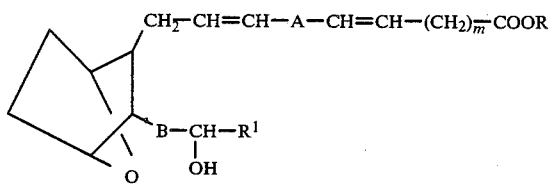

and including all stereoisomers thereof.

The compounds are cardiovascular agents useful, for example, in the treatment of thrombolytic disease.

12 Claims, No Drawings

7-OXABICYCLOHEPTANE SUBSTITUTED PROSTAGLANDIN ANALOGS USEFUL IN THE TREATMENT OF THROMBOLYTIC DISEASE

DESCRIPTION OF THE INVENTION

The present invention relates to 7-oxabicycloheptane substituted prostaglandin analogs which are cardiovascular agents useful, for example, in the treatment of thrombolytic disease. These compounds have the structural formula

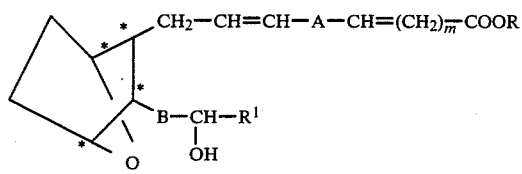

and including all stereoisomers thereof, wherein

A is a single bond or —$CH_2$—; m is 0 when A is $CH_2$ and m is 1 when A is a single bond; R is H, lower alkyl or alkali metal; B is —CH=CH— or —$(CH_2)_2$—; and $R^1$ is lower alkyl, aryl, aralkyl, cycloalkyl, cycloalkylalkyl or lower alkenyl.

Thus, the compounds of formula I of the invention encompass two basic types of compounds which have the following structures:

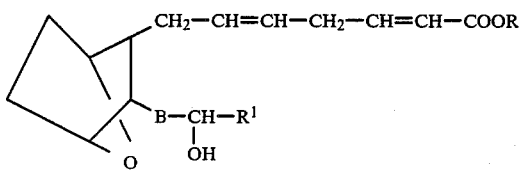

and

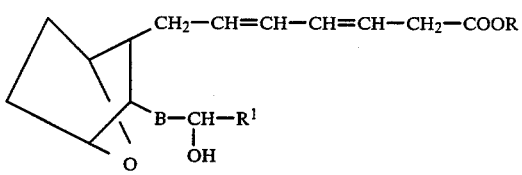

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), and/or 1 or 2 lower alkoxy groups.

The term "aralkyl", "aryl-alkyl" or "aryl-lower alkyl" as used herein refers to lower alkyl groups as discussed above having an aryl substituent, such as benzyl.

The term "lower alkenyl" or "alkenyl" includes straight or branched chain radicals of from 2 to 12 carbons, preferably 2 to 6 carbons in the normal chain, which include one double bond in the normal chain, such as ethenyl, 2-propenyl, 3-butenyl, 2-butenyl, 1-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

Preferred are those compounds of formula I wherein A is a single bond, and m is 1 or A is $CH_2$ and m is 0, B is CH—CH, R is H, and $R^1$ is lower alkyl, aryl, such as phenyl, or aralkyl such as benzyl.

The various compounds of the invention may be prepared as outlined below.

The compounds of formula I of the invention may be prepared as described below.

The starting allylic alcohol VIII or IX may be prepared according to the following reaction sequence.

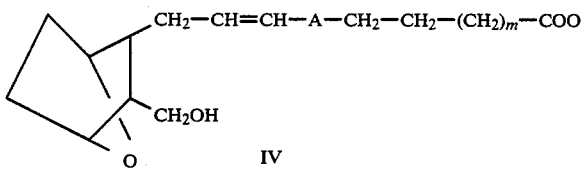 Collins oxidation →

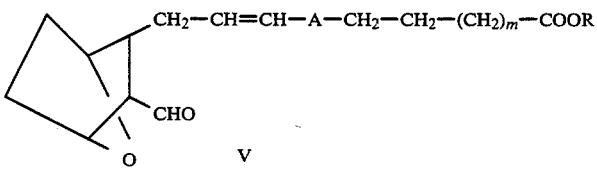

(R is lower alkyl)

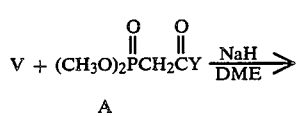
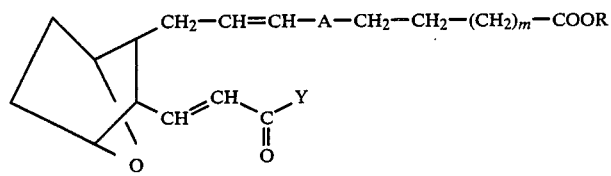

VI (where A is CH₂ or a single bond)

(R is a lower alkyl group throughout)

(B is (CH₂)₂)    (1) NaAl(OCH₂CH₂OCH₃)₂H, CuBr
(2) NaBH₄ + CeCl₃ (0.25–1.5 hrs)

NaBH₄ + CeCl₃ (0.25–1.5 hours)

(B is —CH=CH—)

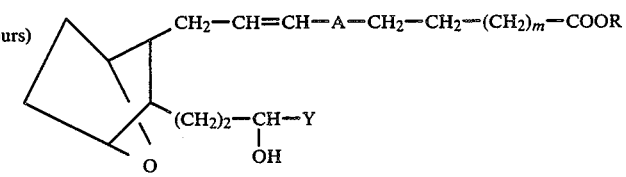

VII

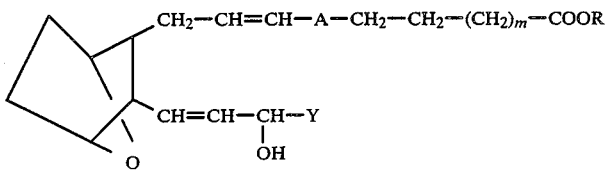

VIII

The starting lower alkyl ester containing the hydroxymethyl group (that is, compound IV) (prepared as described in U.S. Pat. No. 4,143,054) is used to form the aldehyde V. Thus, to form aldehyde V, compound IV is subjected to a Collins oxidation, for example, by reacting IV with chromium oxide in pyridine.

Aldehyde V of the structure

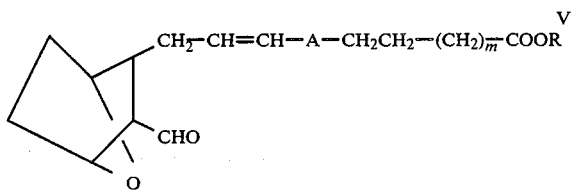

wherein R is lower alkyl is reacted with a dialkoxy phosphonate, such as of the structure

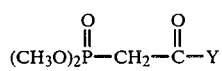

employing a molar ratio of V:A of within the range of from about 1:1 to about 0.5:1, under basic conditions, such as in the presence of sodium hydride or lithium diisopropylamide and an inert organic solvent, such as dimethoxyethane (DME), ether, tetrahydrofuran or toluene to form a compound of the structure

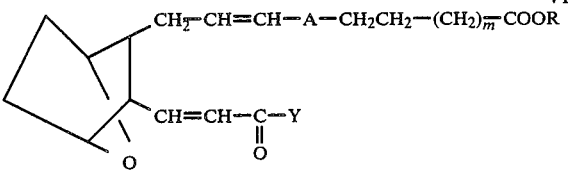

Compound VI may then be reduced by two different ways as outlined above to form compounds VII or VIII

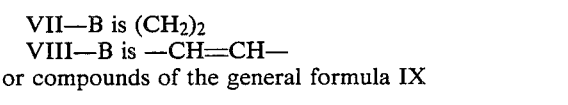

VII—B is (CH₂)₂
VIII—B is —CH=CH—
or compounds of the general formula IX

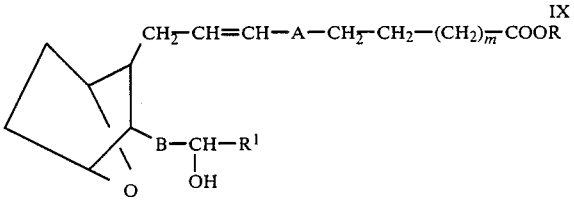

The allylic alcohol IX is made to undergo tetrahydropyranyl ether formation by reacting allylic alcohol IX with dihydropyran in the presence of an inert organic solvent such as methylene chloride or ether and catalytic amounts of p-toluene sulfonic acid at reduced temperatures of from about 0° C. to about 10° C., to form the tetrahydropyranyl ether of formula X

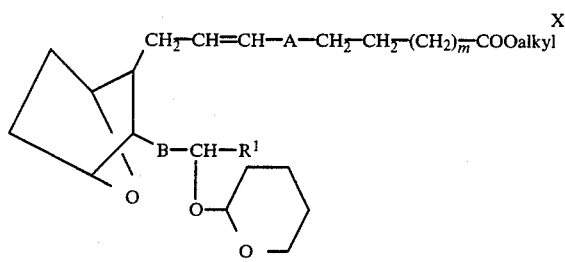

The tetrahydropyranyl ether X is then subjected to phenylselenylation by reacting X with lithium diisopropylamide at reduced temperatures of from about −78° C. to about 0° C. in the presence of an inert organic solvent such as tetrahydrofuran, ether; thereafter a solution of diphenyl-diselenide in an inert organic solvent as described above is added and the reaction is maintained at reduced temperatures as described above to form the selenophenyl ester XI

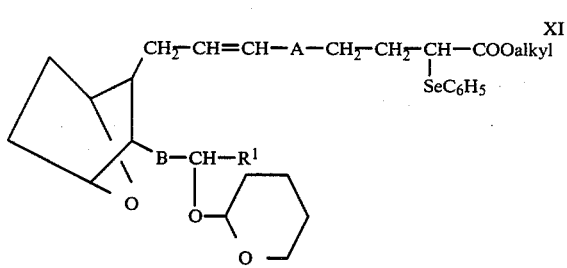

Where compounds of formula I of the invention wherein A is a single bond and m is 1 are desired, that is

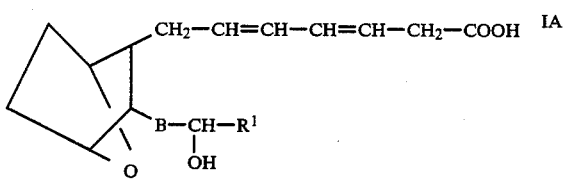

the selenophenyl ester XI where A is a single bond is made to undergo a selenoxide elimination reaction wherein the selenophenyl ester XI in a cooled alcohol solvent and/or ethyl acetate is reacted with hydrogen peroxide at reduced temperatures of from about 0° C. to about 25° C., to form the α,β-unsaturated ester XII

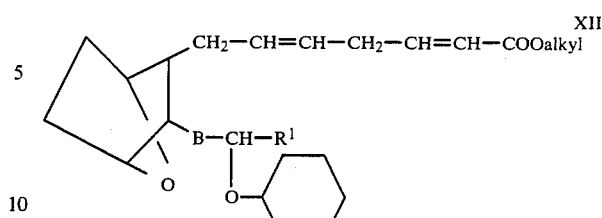

which is then hydrolyzed by reaction with a strong acid such as HCl, Amberlyst Resin or acetic acid in the presence of dimethoxyethane, tetrahydrofuran or other inert solvent to form the ester IB

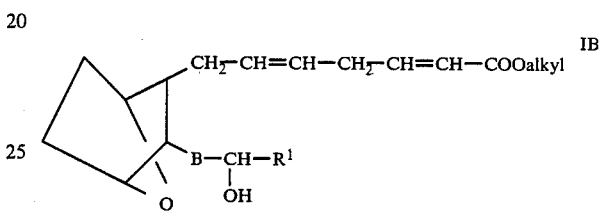

The ester IB is then hydrolyzed by treatment with a base such as lithium hydroxide, potassium carbonate or sodium hydroxide in the presence of an inert organic solvent such as tetrahydrofuran, methanol or dimethoxyethane-water to form the corresponding alkali metal salt which is then treated with strong acid such as HCl to form the acid compound of the invention.

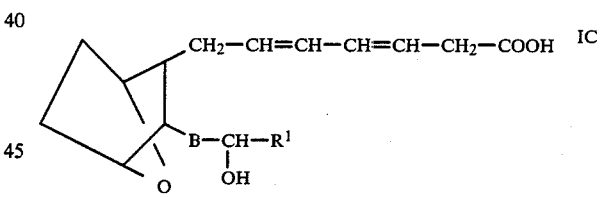

Where compounds of formula I of the invention wherein A is $CH_2$ and m is 0 are desired, that is

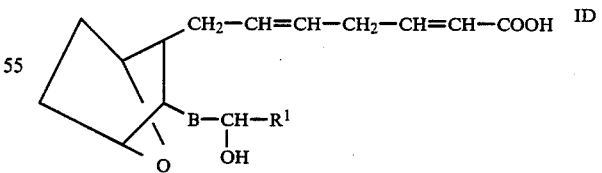

the selenophenyl ester XI is hydrolyzed by treatment with a base such as lithium hydroxide, potassium carbonate or sodium hydroxide in the presence of an inert organic solvent such as tetrahydrofuran, methanol or dimethoxyethane-water and then with a strong acid such as HCl to form the acid XIII

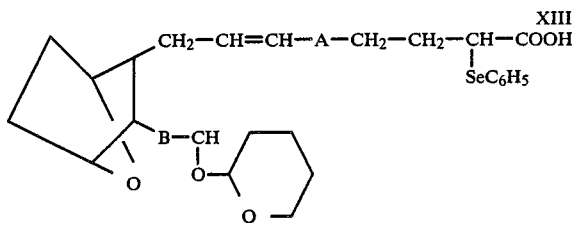

Acid XIII is then oxidized by reaction with hydrogen peroxide in the presence of an inert organic solvent such as tetrahydrofuran at reduced temperatures of from about 0° C. to about 25° C. to form the $\alpha,\beta$-unsaturated acid XIV

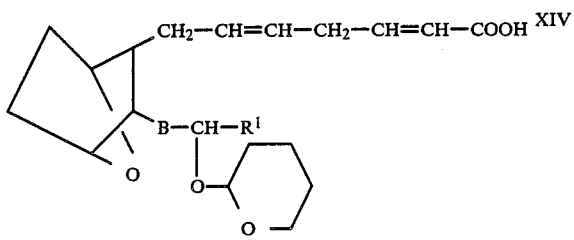

which is then hydrolyzed by treatment with strong acid such as HCl in the presence of an inert organic solvent such as dimethoxyethane-water to form acid IE

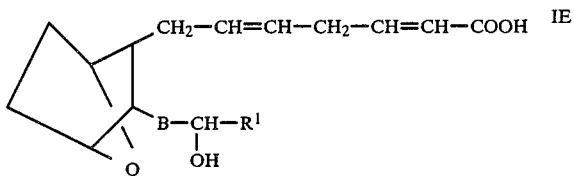

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

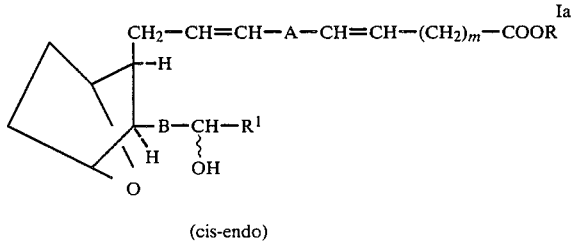

(cis-endo)

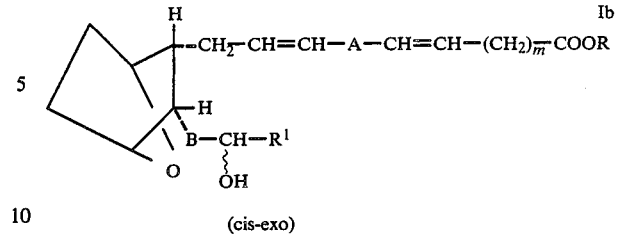

(cis-exo)

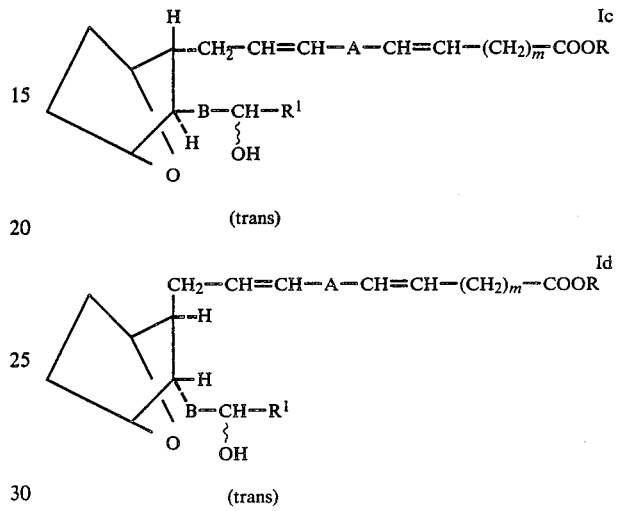

The wavy line ( $\wr$ ) in the above formulae indicates that the hydroxy group in each of the compounds of formulae Ia-Id is either R($\beta$) or S($\alpha$).

The nucleus in each of the compounds of the invention is depicted as

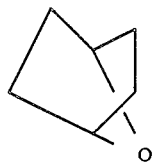

for matter of convenience; it will also be appreciated that the nucleus in the compounds of the invention may be depicted as

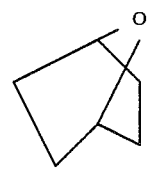

The compounds of this invention are cardiovascular agents useful as platelet aggregation inhibitors, such as inhibiting arachidonic acid-induced platelet aggregation (e.g., for treatment of thrombolytic disease, such as coronary or cerebral thromboses) and in inhibiting bronchoconstriction as induced by asthma. They are also selective thromboxane $A_2$ receptor antagonists and synthetase inhibitors, e.g., having a vasodilatory effect for treatment of myocardial ischemic disease, such as angina pectoris.

The compounds of the invention can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in degrees Centigrade.

EXAMPLE 1

[1α,2β(5Z),3β(1E,3R,4S),4α]-7-[3-(3-Hydroxy-4-phenyl-1-pentenyl)-7-oxabicyclo[2.2.1]hept-2-yl]-3,5-heptadienoic acid

A.

[1α,2β(Z),3β(1E),4α]-7-[3-(3-Hydroxy-4-phenyl-1-pentenyl)-7-oxabicyclo[2.2.1]hept-2-yl]-5-heptenoic acid, methyl ester

(1) (+) Methyl 2-phenylpropionate (+) 2-Phenylpropionic acid (8.4 g, 56 mmol) in methanol (180 ml) and concentrated $H_2SO_4$ (2 ml) were heated at reflux for 4 hours. The reaction was cooled down to room temperature and concentrated in vacuo (~100 ml). The products were extracted with $Et_2O$ (150 ml×3), which was washed with saturated $NaHCO_3$, $H_2O$ and dried over $MgSO_4$. Filtration and evaporation of solvent yielded a yellow oil (8.9 g), which was distilled to give (+) methyl 2-phenylpropionate as a colorless oil (8.34 g, 51 mmol, 91%, b.p. 73° C./1.5 mm Hg), $[α]^D = +111°$ (c=2, toluene).

(2) (+) 2-Oxo-3-phenylbutyl dimethyl phosphonate n-Butyllithium (1.6M, 62.5 ml, 100 mmol) was added dropwise to a magnetically stirred solution of dimethylmethyl phosphonate (12.4 g, 100 mmol) in THF (90 ml) at −78° C. Stirring was continued for 30 minutes at −78° C. Then ester (8.2 g, 50 mmol) was added dropwise to give a yellow colored solution. After 3 hours stirring at −78° C., the reaction was warmed to room temperature and stirred for 1 hour. The reaction was quenched by addition of acetic acid to pH 5~6. The solvent was removed in vacuo and $H_2O$ (100 ml) was added. The products were extracted with $CH_2Cl_2$ (100 ml×3), which was washed with saturated $NaHCO_3$, $H_2O$ and dried over $MgSO_4$. Filtration and evaporation of solvent left a yellow oil. This was fractionated to give (+)-2-oxo-3-phenylbutyl dimethyl phosphonate (8.1 g, 31.6 mmol, 63%, b.p. 142°-144°/0.2 mm Hg), $[α]^D = +235°$ (c=2, toluene).

(3)

[1α,2β(Z),3β(1E,4S),4α]-7-[3-(3-Oxo-4-phenyl-1-pentenyl)-7-oxabicyclo[2.2.1]hept-2-yl]-5-heptenoic acid, methyl ester Sodium hydride (201 mg of 50% in mineral oil, 4.18 mmol) was suspended in distilled dimethoxyethane (70 ml) in an argon atmosphere and treated with a solution of Part A(2) phosphonate (1.45 g, 4.7 mmol) in DME (10 ml). The mixture was stirred at room temperature 90 minutes. A solution of (+)-[1α,2β(Z),3β,4α]-7-[3-formyl-7-oxabicyclo[2.2.1]hept-2-yl]-5-heptenoic acid, methyl ester (prepared as described in U.S. Pat. No. 4,143,054) (1.031 g, 3.8 mmol) in DME (5 ml) was then added and the mixture was stirred overnight at room temperature. The reaction was quenched by adding glacial acetic acid (0.5 ml) and the solvent was removed in vacuo. Ether and saturated $NaHCO_3$ were added and the layers were separated. The ether layer was washed once with saturated $NaHCO_3$ solution, dried over $MgSO_4$, filtered and taken to dryness in vacuo leaving a viscous oil. This was chromatographed on silica gel 60 (110 g), eluting with ether-pet ether (2:3) to give 992 mg (66%) of title A (3) compound as an oil. A faster moving material (98 mg, 6.5%) was also isolated and identified by $^1H$ NMR as the cis double bond isomer.

(4)

[1α,2β(Z),3β(1E),4α]-7-[3-(3-Hydroxy-4-phenyl-1-pentenyl)-7-oxabicyclo[2.2.1]hept-2-yl]-5-heptenoic acid, methyl ester Title compound from Part A (3) (0.99 g, 2.49 mmol) and $CeCl_3.7.6H_2O$ (0.954 g, 2.49 mmol) were dissolved in methanol (25 ml) and THF (2 ml). The solution was cooled in an ice bath and $NaBH_4$ (94.1 mg, 2.5 mmol) was added portionwise in 30 seconds. The ice bath was removed and the mixture was stirred 10 minutes, then poured into saturated $NH_4Cl$ solution (200 ml). The product was extracted into ethyl acetate (5×50 ml). The combined ethyl acetate extracts were dried ($MgSO_4$), filtered, and freed of solvent in vacuo to give a viscous oil (0.953 g). This was chromatographed on silica gel 60 (60 g) eluting with ether-pet ether (3:2) to give 616 mg of nearly clean faster moving isomer and 150 mg (15%) of slower moving isomer. TLC's silica gel; $Et_2O$-pet ether 3:2; vanillin $R_f$'s 0.35 and 0.25. The faster moving isomer was rechromatographed eluting with the same solvent to give 605 mg (61%) of title A compound.

B.

[1α,2β(Z),3β(1E,4S),4α]-7-[3-(3-Tetrahydropyranyloxy-4-phenyl-1-pentenyl)-7-oxabicyclo[2.2.1]hept-2-yl]-5-heptenoic acid, methyl ester To a solution of 2.16 g of title A chiral allylic alcohol (3.4 mmole) in 20 ml of dry methylene chloride was added with stirring a catalytic amount of p-toluene sulfonic acid, followed by 750 μl of dihydropyran (8.33 mmole) at 0°-5° C. The reaction mixture was stirred at 0°-5° C. for 40 minutes whereupon it was washed with aqueous sodium bicarbonate solution. The methylene chloride layer was separated and the aqueous layer was extracted with ether. The combined organic extract was dried over anhydrous magnesium sulfate and concentrated under reduced pressure. Purification by flash chromatography on a silica gel column gave 2.43 g of desired title THP-ether (eluting solvent 10-15% ethyl acetate in hexane).

C.
[1α,2β(Z),3β(1E,3R,4S),4α]-7-[3-(3-Tetrahydropyranyloxy-4-phenyl-1-pentenyl)-7-oxabicyclo[2.2.1]hept-2-yl]-2-selenophenyl-5-heptenoic acid, methyl ester To a solution of 2 ml of distilled diisopropylamine (13 mmole, distilled over CaH$_2$) in 30 ml of dry THF, cooled at −78° C. in a dry ice-acetone bath was added dropwise 7.5 ml of a 1.6M solution of n-butyllithium in hexane (12 mmole). The solution of lithium diisopropylamide so formed was stirred at −78° C. for 30 minutes, whereupon a solution of 2.43 g of title B THP-ether (5 mmole) in 15 ml of dry THF was added dropwise over a period of 10 minutes. The colorless solution was stirred at −78° C. for an additional 30 minutes, whereupon a solution of 3.75 g of diphenyl-diselenide (12 mmole) in 5 ml of dry THF was added dropwise. Initially the yellow color of diselenide discharged immediately upon addition. The yellow solution was stirred at −78° C. for 30 minutes, whereupon the cooling bath was removed. After 30 minutes the reaction mixture was quenched by addition of aqueous ammonium chloride solution. It was then diluted with water and the organic layer was separated. The aqueous layer was extracted with ether. The combined organic extract was dried over anhydrous magnesium sulfate and concentrated under reduced pressure. The crude residue was chromatographed on a silica gel column. Elution with 5–15% ethyl acetate in hexane gave 2.6 g of title α-selenophenyl ester as a colorless oil.

D.
[1α,2β(2E,5Z),3β(1E,3R,4S),4α]-7-[3-(3-Tetrahydropyranyloxy-4-phenyl-1-pentenyl)-7-oxabicyclo[2.2.1]hept-2-yl]-2,5-heptadienoic acid, methyl ester To a solution of 600 mg of title C seleno ester (0.94 mmole) in 6 ml of ethyl acetate and 4 ml of methanol, cooled in an ice-water bath was added with stirring 1 ml of a 30% aqueous hydrogen peroxide solution. After 30 minutes at 0°–5° C., the reaction mixture was warmed to room temperature and stirred for an additional one hour. The reaction mixture was diluted with ether and washed with water. The organic layer was dried over anhydrous magnesium sulfate and concentrated under reduced pressure. The crude residue was chromatographed on a silica gel column and eluted with 10–20% ethyl acetate in hexane to obtain 320 mg of title α,β-unsaturated ester.

E.
[1α,2β(2E,5Z),3β(1E,3R,4S),4α]-7-[3-(3-Hydroxy-4-phenyl-1-pentenyl)-7-oxabicyclo[2.2.1]hept-2-yl]-2,5-heptadienoic acid, methyl ester To a solution of 320 mg of title D α,β-unsaturated ester in 10 ml of distilled dimethoxyethane (DME) was added with stirring 3 ml of a 2N aqueous hydrochloric acid solution. The reaction mixture was stirred under an argon atmosphere for 24 hours, whereupon it was diluted with ether and washed with water. The organic extract was dried over anhydrous magnesium sulfate and concentrated under reduced pressure. The crude residue was chromatographed on a silica gel column and eluted with 20–30% ethyl acetate in hexane to obtain 245 mg of title methyl ester.

F.
[1α,2β(5Z),3β(1E,3R,4S),4α]-7-[3-(3-Hydroxy-4-phenyl-1-pentenyl)-7-oxabicyclo[2.2.1]hept-2-yl]-3,5-heptadienoic acid To a solution of 245 mg of title E methyl ester (0.62 mmole) in 4 ml of distilled THF and 1 ml of water was added with stirring 1.5 ml of a 1N aqueous lithium hydroxide solution. The reaction mixture was stirred at room temperature for 4 hours, whereupon it was acidified to pH 0.5 by addition of 2N aqueous hydrochloric acid solution.

The reaction mixture was extracted with ether (x2). The combined ether extract was dried over anhydrous magnesium sulfate and concentrated under reduced pressure. The crude oily residue was chromatographed on a CC-7 silica gel column. Elution with 20–50% ethyl acetate in hexane gave 220 mg of desired title acid.

Anal Calcd for C$_{24}$H$_{30}$O$_4$: C, 75.36; H, 7.91 Found: C, 75.74; H, 7.73

TLC—R$_f$0.19 (50% ethyl acetate in hexane)

EXAMPLE 2
[1S-[1α,2β(2E,5Z),3β(1E,3R,4S),4α]]-7-[3-(3-Hydroxy-4-phenyl-1-pentenyl)-7-oxabicyclo[2.2.1]hept-2-yl]-2,5-heptadienoic acid

A.
[1α,2β(Z),3β(1E,3R,4S),4α]-7-[3-(3-Tetrahydropyranyloxy-4-phenyl-1-pentenyl)-7-oxabicyclo[2.2.1]hept-2-yl]-2-selenophenyl-5-heptenoic acid To a solution of 1.36 g Example 1 Part C seleno-ester (∼2 mmole) in 12 ml of distilled THF and 3 ml of water was added with stirring 9 ml of a 1N aqueous lithium hydroxide solution. The heterogeneous reaction mixture was stirred at room temperature under an argon atmosphere for 2 days, whereupon it was acidified by careful addition of 2N aqueous hydrochloric acid solution. Extraction with ether (X3), drying of the ether extract over anhydrous magnesium sulfate and finally concentration under reduced pressure gave 1.27 g of desired title acid as a colorless oil.

B.
[1α,2β(2E,5Z),3β(1E,3R,4S),4α]-7-[3-(3-Tetrahydropyranyloxy-4-phenyl-1-pentenyl)-7-oxabicyclo[2.2.1]hept-2-yl]-2,5-heptadienoic acid A solution of 423 mg of title A α-selenophenyl acid (0.68 mmole) in 10 ml of distilled THF was treated with 500 μl of a 30% aqueous hydrogen peroxide solution at 0°–5° C. After a few minutes, the cooling bath was removed and the reaction mixture was stirred at room temperature for one hour. It was then diluted with ether and washed several times with water. The organic extract was dried over anhydrous magnesium sulfate and concentrated under reduced pressure. The crude oil was chromatographed on a CC-7 silica gel column and eluted with 20–50% ethyl acetate in hexane to obtain 260 mg of title acid (contained ∼10% of title C acid).

C.
[1S-[1α,2β(2E,5Z),3β(1E,3R,4S),4α]]-7-[3-(3-Hydroxy-4-phenyl-1-pentenyl)7-oxabicyclo[2.2.1]hept-2-yl]-2,5-heptadienoic acid A solution of 260 mg of title B α,β-unsaturated acid in 10 ml of dimethoxy ethane was treated at room temperature with 3 ml of a 2N aqueous hydrochloric acid solution. After stirring at room temperature for 8 hours, the reaction mixture was diluted with ether and washed thoroughly with water. The aqueous layer was re-extracted with ether twice. The combined organic extract was dried over anhydrous magnesium sulfate and concentrated under reduced pressure. The crude residue was chromatographed on a CC-7 silica gel column and eluted with 20–50% ethyl acetate in hexane to obtain 170 mg of title 2,3-dehydro acid as a foam.

Anal Calcd for $C_{24}H_{30}O_4$*: C, 74.64; H, 7.93 Found: C, 74.64; H, 7.85 (*contains 0.2 mole of water).

TLC—$R_f$ 0.20 (50% ethyl acetate in hexane)

EXAMPLE 3

[1S-[1α,2β(5Z),3β(1E,3R,4S),4α]]-7-[3-(3-Hydroxy-3-phenyl-1-propenyl)-7-oxabicyclo[2.2.1]hept-2-yl]-3,5-heptadienoic acid Following the procedure of Example 1 except substituting benzoic acid for 2-phenylpropionic acid, the title compound is obtained.

EXAMPLE 4

[1S-[1α,2β(5Z),3β(1E,3R,4S),4α]]-7-[3-(3-Hydroxy-4-phenyl-1-butenyl)-7-oxabicyclo[2.2.1]hept-2-yl]-3,5-heptadienoic acid Following the procedure of Example 1 except substituting phenylacetic acid for 2-phenylpropionic acid, the title compound is obtained.

EXAMPLE 5

[1S-[1α,2β(5Z),3β(1E,3R,4S),4α]]-7-[3-(3-Hydroxy-3-cyclohexyl-1-propenyl)-7-oxabicyclo[2.2.1]hept-2-yl]-3,5-heptadienoic acid Following the procedure of Example 1 except substituting cyclohexyl carboxylic acid for 2-phenylpropionic acid, the title compound is obtained.

EXAMPLE 6

[1S-[1α,2β(5Z),3β(1E,3R,4S),4α]]-7-[3-(3-Hydroxy-4-cyclopentyl-1-butenyl)-7-oxabicyclo[2.2.1]hept-2-yl]-3,5-heptadienoic acid Following the procedure of Example 1 except substituting cyclopentylacetic acid for 2-phenylpropionic acid, the title compound is obtained.

EXAMPLE 7

[1S-[1α,2β(5Z),3β(1E,3R,4S),4α]]-7-[3-(3-Hydroxy-1,5-hexadienyl)-7-oxabicyclo[2.2.1]hept-2-yl]-3,5-heptadienoic acid Following the procedure of Example 1 except substituting 2-propenyl carboxylic acid for 2-phenylpropionic acid, the title compound is obtained.

EXAMPLE 8

[1S-[1α,2β(5Z),3β(1E,3R,4S),4α]]-7-[3-(3-Hydroxy-1-nonenyl-7-oxabicyclo[2.2.1]hept-2-yl]-3,5-heptadienoic acid Following the procedure of Example 1 except substituting hexane carboxylic acid for 2-phenylpropionic acid, the title compound is obtained.

EXAMPLE 9

[1S-[1α,2β(5Z),3β(1E,3R,4S),4α]]-7-[3-(3-Hydroxy-1-pentenyl)-7-oxabicyclo[2.2.1]hept-2-yl]-3,5-heptadienoic acid Following the procedure of Example 1 except substituting propionic acid for 2-phenylpropionic acid, the title compound is obtained.

EXAMPLE 10

[1S-[1α,2β(2E,5Z),3β(1E,3R,4S),4α]]-7-[3-(3-Hydroxy-3-phenyl-1-propenyl)-7-oxabicyclo[2.2.1]hept-2-yl]-2,5-heptadienoic acid Following the procedure of Examples 1 and 2 except substituting benzoic acid for 2-phenylpropionic acid, the title compound is obtained.

EXAMPLE 11

[1S-[1α,2β(2E,5Z),3β(1E,3R,4S),4α]]-7-[3-(3-Hydroxy3-cyclohexyl-1-propenyl)-7-oxabicyclo[2.2.1]hept-2-yl]-2,5-heptadienoic acid Following the procedure of Examples 1 and 2 except substituting cyclohexylcarboxylic acid for 2-phenylpropionic acid, the title compound is obtained.

EXAMPLE 12

[1S-[1α,2β(2E,5Z),3β(1E,3R,4S),4α]]-7-[3-(3-Hydroxy-3-cycloheptyl-1-propenyl)-7-oxabicyclo[2.2.1]hept-2-yl]-2,5-heptadienoic acid Following the procedure of Examples 1 and 2 except substituting cycloheptyl carboxylic acid for 2-phenylpropionic acid, the title compound is obtained.

EXAMPLE 13

[1S-[1α,2β(2E,5Z),3β(1E,3R,4S),4α]]-7-[3-(3-Hydroxy-4-cyclopentyl-1-butenyl)-7-oxabicyclo[2.2.1]hept-2-yl]-2,5-heptadienoic acid Following the procedure of Examples 1 and 2 except substituting cyclopentylacetic acid for 2-phenylpropionic acid, the title compound is obtained.

EXAMPLE 14

[1S-[1α,2β(2E,5Z),3β(1E,3R,4S),4α]]-7-[3-(3-Hydroxy-1,6-heptadienyl)-7-oxabicyclo[2.2.1]hept-2-yl]-2,5-heptadienoic acid Following the procedure of Examples 1 and 2 except substituting 3-butenyl carboxylic acid for 2-phenylpropionic acid, the title compound is obtained.

EXAMPLE 15

[1S-[1α,2β(2E,5Z),3β(1E,3R,4S),4α]]-7-[3-(3-Hydroxy-1-hexenyl)-7-oxabicyclo[2.2.1]hept-2-yl]-2,5-heptadienoic acid Following the procedure of Examples 1 and 2 except substituting propionic acid for 2-phenylpropionic acid, the title compound is obtained.

EXAMPLE 16

[1α,2β(5Z),3β(3R,4S),4α]-7-[3-(3-Hydroxy-4-phenyl-1-pentyl)-7-oxabicyclo[2.2.1]hept-2-yl]-3,5-heptadienoic acid

A.

[1S-[1α,2β(Z),3β(4S),4α]]-7-[3-(3-Oxo-4-phenyl-1-pentyl)-7-oxabicyclo[2.2.1]hept-2-yl]-5-heptenoic acid, methyl ester To a suspension of 686 mg of purified cuprous bromide (4.8 mmole) in 12 ml of dry THF, cooled at 0°–5° C. was added with stirring 1.35 ml of a 3.5M solution of red-Al (sodium bis(2-methoxyethoxy)aluminumhydride) in toluene dropwise. The solution was stirred at 0°–5° C. for 30 minutes, whereupon it was cooled to −78° C. and 2 ml of n-butanol (18 mmole) was added rapidly, followed by a solution of 476 mg of Example 1 Part A (3) enone (1.2 mmole) in 4 ml of dry THF. After 10 minutes at −78° C., the reaction mixture was warmed to −20° C. and left for an additional one hour. The reaction mixture was quenched by addition of 70 ml of water and then poured into saturated ammonium chloride solution and was extracted with ether (x3). The ether extract was dried over anhydrous magnesium sulfate, filtered and the filtrate was concentrated under reduced pressure. 480 Mg of desired title ketone was obtained (100% yield) as a colorless oil.

B.

[1S-[1α,2β(Z),3β(3R,4S),4α]]-7-[3-(3-Hydroxy-4-phenyl-1-pentyl)-7-oxabicyclo[2.2.1]hept-2-yl]-5-heptenoic acid, methyl ester To a solution of 400 mg of title A ketone (1 mmole) in 2 ml of methanol and 2 ml of dry THF is added with stirring 400 mg of ceric (III) chloride hydrate (1 mmole). After stirring at room temperature for 10 minutes, the reaction mixture is cooled to −50° C. and 40 mg of solid sodium borohydride (~1 mmole) is added to the reaction mixture. The reaction mixture is stirred at −50° C. for 45 minutes, whereupon 5 ml of acetone is added to destroy excess of borohydride. The mixture is stirred for an additional 5 minutes at −50° C. The cooling bath is removed and the reaction mixture is evaporated to dryness. The crude residue is diluted with ether and washed with 1N aqueous hydrochloric acid solution. The ether extract is dried over anhydrous MgSO4 and concentrated under reduced pressure. The crude residue is chromatographed on a silica gel column and eluted with 30–50% ethyl acetate in hexane to obtain the desired title 3R-alcohol.

C.

[1α,2β(5Z),3β(3R,4S),4α]-7-[3-(3-Hydroxy-4-phenyl-1-pentyl)-7-oxabicyclo[2.2.1]hept-2-yl]-3,5-heptadienoic acid Following the procedure of Example 1 except substituting the Part B alcohol for the Example 1 Part A alcohol, the title compound is obtained.

EXAMPLE 17

[1α,2β(2E,5Z),3β(3R,4S),4α]-7-[3-(3-Hydroxy-4-phenyl-1-pentyl)-7-oxabicyclo[2.2.1]hept-2-yl]-2,5-heptadienoic acid Following the procedure of Example 16, Example 1 Parts A to C and Example 2, except substituting the Example 16 Part B alcohol for the Example 1 Part A alcohol, the title compound is obtained.

EXAMPLE 18

[1S-[1α,2β(5Z),3β(4S),4α]]-7-[3-(3-Hydroxy-3-phenyl-1-propyl)-7-oxabicyclo[2.2.1]hept-2-yl]-3,5-heptadienoic acid Following the procedure of Example 16 and Example 1 except substituting benzoic acid for 2-phenylpropionic acid, the title compound is obtained.

EXAMPLE 19

[1S-[1α,2β(5Z),3β(4S),4α]]-7-[3-(3-Hydroxy-4-phenyl-1-butyl)-7-oxabicyclo[2.2.1]hept-2-yl]-3,5-heptadienoic acid Following the procedure of Example 16 and Example 1 except substituting phenylacetic acid for 2-phenylpropionic acid, the title compound is obtained.

EXAMPLE 20

[1S-[1α,2β(5Z),3β(4S),4α]]-7-[3-(3-Hydroxy-3-cyclohexyl-1-propyl)-7-oxabicyclo[2.2.1]hept-2-yl]-3,5-heptadienoic acid Following the procedure of Example 16 and Example 1 except substituting cyclohexylcarboxylic acid for 2-phenylpropionic acid, the title compound is obtained.

EXAMPLE 21

[1S-[1α,2β(5Z),3β(4S),4α]]-7-[3-(3-Hydroxy-4-cyclopentyl-1-butyl)-7-oxabicyclo[2.2.1]hept-2-yl]-3,5-heptadienoic acid Following the procedure of Example 16 and Example 1 except substituting cyclopentylacetic acid for 2-phenylpropionic acid, the title compound is obtained.

EXAMPLE 22

[1S-[1α,2β(5Z),3β(4S),4α]]-7-[3-(3-Hydroxy-5-hexenyl)-7-oxabicyclo[2.2.1]hept-2-yl]-3,5-heptadienoic acid Following the procedure of Example 16 and Example 1 except substituting 2-propenyl carboxylic acid for 2-phenylpropionic acid, the title compound is obtained.

EXAMPLE 23

[1S-[1α,2β(5Z),3β(4S),4α]]-7-[3-(3-Hydroxy-1-nonyl)-7-oxabicyclo[2.2.1]hept-2-yl]-3,5-heptadienoic acid Following the procedure of Example 16 and Example 1 except substituting hexanecarboxylic acid for 2-phenylpropionic acid, the title compound is obtained.

EXAMPLE 24

[1S-[1α,2β(2E,5Z),3β(4S),4α]]-7-[3-(3-Hydroxy-3-phenyl-1-propyl)-7-oxabicyclo[2.2.1]hept-2-yl]-2,5-heptadienoic acid Following the procedure of Examples 16, 17 and Example 1 Parts A to C and Example 2 except substituting benzoic acid for 2-phenylpropionic acid, the title compound is obtained.

EXAMPLE 25

[1S-[1α,2β(2E,5Z),3β(4S),4α]]-7-[3-(3-Hydroxy-4-phenyl-1-butyl)-7-oxabicyclo[2.2.1]hept-2-yl]-2,5-heptadienoic acid Following the procedure of Examples 16, 17 and Example 1 Parts A to C and Example 2 except substituting phenylacetic acid for 2-phenylpropionic acid, the title compound is obtained.

EXAMPLE 26

[1S-[1α,2β(2E,5Z),3β(4S),4α]]-7-[3-(3-Hydroxy-3-cyclohexyl-1-propyl)-7-oxabicyclo[2.2.1]hept-2-yl]-2,5-heptadienoic acid Following the procedure of Examples 16, 17 and Example 1 Parts A to C and Example 2 except substituting cyclohexyl carboxylic acid for 2-phenylpropionic acid, the title compound is obtained.

EXAMPLE 27

[1S-[1α,2β(2E,5Z),3β(4S),4α]]-7-[3-(3-Hydroxy-1-hexyl)-7-oxabicyclo[2.2.1]hept-2-yl]-2,5-heptadienoic acid Following the procedure of Examples 16, 17 and Example 1 Parts A to C and Example 2 except substituting propionic acid for 2-phenylpropionic acid, the title compound is obtained.

What is claimed is:

1. A compound having the structural formula

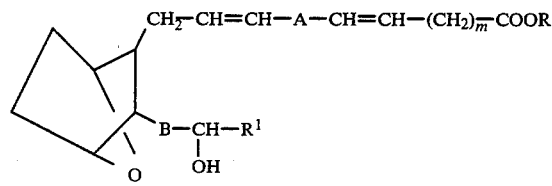

and including all stereoisomers thereof;
wherein
A is a single bond or —$CH_2$—; m is 0 when A is —$CH_2$— and m is 1 when A is a single bond; B is —CH=CH— or $(CH_2)_2$; R is H, lower alkyl or alkali metal; and $R^1$ is lower alkyl, aryl, aralkyl, cycloalkyl, cycloalkylalkyl or lower alkenyl, wherein the term lower alkyl or alkyl by itself or as part of another group contains 1 to 12 carbons and is unsubstituted or substituted with halo, trifluoromethyl, alkoxy, aryl, alkyl-aryl, haloaryl, cycloalkyl or alkylcycloalkyl;
the term aryl by itself or as part of another group contains 6 to 10 carbons and is unsubstituted or substituted with 1 or 2 lower alkyl groups, 1 or 2 halogens and/or 1 or 2 lower alkoxy groups;
the term cycloalkyl by itself or as part of another group contains 3 to 12 carbons and is unsubstituted or substituted with 1 or 2 halogens, 1 or 2 lower alkyl groups and/or 1 or 2 lower alkoxy groups; and
the term lower alkenyl by itself or as part of another group contains 2 to 12 carbons.

2. The compound as defined in claim 1 wherein A is a single bond and m is 1.

3. The compound as defined in claim 1 wherein A is —$CH_2$— and m is 0.

4. The compound as defined in claim 1 wherein B is —CH=CH—.

5. The compound as defined in claim 4 wherein $R^1$ is butyl, pentyl, hexyl, heptyl or 1,1-dimethylpentyl.

6. The compound as defined in claim 1 having the name [1S-[1α,2β(5Z),3β(1E,3R,4S),4α]]-7-[3-(3-hydroxy-4-phenyl-1-pentenyl)-7-oxabicyclo[2.2.1]hept-2-yl]-3,5-heptadienoic acid or the methyl or ethyl ester thereof, including all stereoisomers thereof.

7. The compound as defined in claim 1 having the name [1S-[1α,2β(2E,5Z),3β(1E,3R,4S),-4α]]-7-[3-(3-hydroxy-4-phenyl-1-pentenyl)-7-oxabicyclo[2.2.1]hept-2-yl]-2,5-heptadienoic acid including all stereoisomers thereof.

8. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

9. The method as defined in claim 8 wherein said compound is administered in an amount within the range of from about 1 to about 100 mg/kg.

10. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier thereof.

11. A method of inhibiting bronchoconstriction associated with asthma, which comprises administering to a mammalian host an effective amount of a compound as defined in claim 1 or a pharmaceutically acceptable salt thereof.

12. A method for treating peripheral vascular disease, which comprises topically or systemically administering to a mammalian host an effective amount of a compund as defined in claim 1 or a pharmaceutically acceptable salt thereof.

* * * * *

UNITED STATES PATENT AND TRADEMARK OFFICE
CERTIFICATE OF CORRECTION

PATENT NO. : 4,536,514

DATED : August 20, 1985

INVENTOR(S) : Jagabandhu Das et al.

It is certified that error appears in the above-identified patent and that said Letters Patent is hereby corrected as shown below:

Column 1, line 15, structure I should read

-- 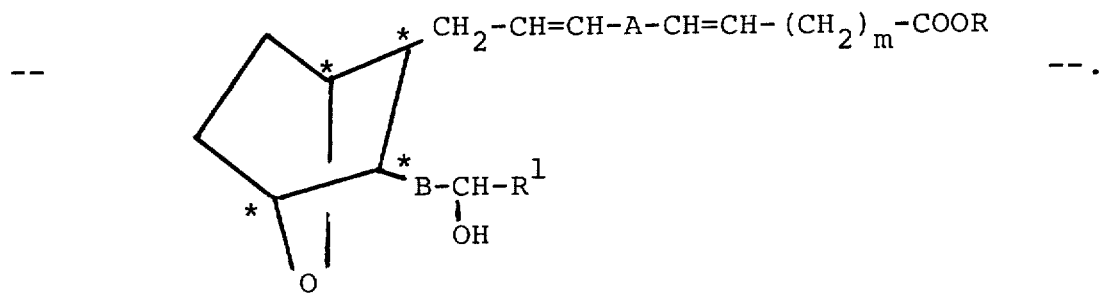 --.

Column 10, line 56, "3.4" should read --5.4--.

Signed and Sealed this

Eleventh Day of November, 1986

Attest:

DONALD J. QUIGG

Attesting Officer     Commissioner of Patents and Trademarks